(12) United States Patent
Dalla Zorza et al.

(10) Patent No.: US 10,576,109 B2
(45) Date of Patent: Mar. 3, 2020

(54) ***PROPIONIBACTERIUM ACNES* AND *GRANULOSUM* PARIETAL FRACTION HAVING IMMUNOMODULATING ACTION**

(71) Applicant: DEPOFARMA S.P.A., Preganziol (IT)

(72) Inventors: Paola Dalla Zorza, Mira (IT); Alessandra Dalla Zorza, Preganziol (IT)

(73) Assignee: DEPOFARMA S.P.A., Preganziol (IT)

( * ) Notice: Subject to any disclaimer, the term of this patent is extended or adjusted under 35 U.S.C. 154(b) by 0 days.

(21) Appl. No.: 15/326,265

(22) PCT Filed: Jul. 16, 2015

(86) PCT No.: PCT/IB2015/055377
§ 371 (c)(1),
(2) Date: Jan. 13, 2017

(87) PCT Pub. No.: WO2016/009377
PCT Pub. Date: Jan. 21, 2016

(65) Prior Publication Data
US 2017/0202886 A1  Jul. 20, 2017

(30) Foreign Application Priority Data
Jul. 16, 2014 (IT) .............. MI2014A1298

(51) Int. Cl.
*A61K 35/74* (2015.01)
*C12N 1/20* (2006.01)
*C12N 1/06* (2006.01)

(52) U.S. Cl.
CPC .............. *A61K 35/74* (2013.01); *C12N 1/066* (2013.01); *C12N 1/20* (2013.01)

(58) Field of Classification Search
None
See application file for complete search history.

(56) References Cited

FOREIGN PATENT DOCUMENTS

| GB | 1476422 | 6/1977 |
| WO | 00/40269 A2 | 7/2000 |

OTHER PUBLICATIONS

Buck et al., "Investigation of the Component of Propionibacterium acnes (Corynebacterium parvum) Responsible for Macrophage Activation", Infection and Immunity 27: 620-627 (1980).
Kirchner et al., "Protection Against Herpes Simplex Virus Infection in Mice by Corynebacterium parvum", Infection and Immunity 16: 9-11 (1977).
Ohashi et al., "Mode of Protection of Mice against Herpes Simplex Virus Type 2 Infection by Propionibacterium", Microbiol. Immunol. 27: 601-609 (1983).
Sher et al., "Effects of BCG, Corynebacterium parvum, and Methanol-Extraction Residue in the Reduction of Mortality from *Staphylococcus aureus* and Candida albicans Infections in Immunosuppressed Mice", Infection and Immunity 12: 1325-1330 (1975).

*Primary Examiner* — Robert A Zeman
(74) *Attorney, Agent, or Firm* — Jeffrey N. Townes; Cozen O'Connor

(57) ABSTRACT

The present invention relates to a free parietal fraction of *Propionibacterium acnes* and *granulosum*, obtained by delipidation and controlled crushing of the strain ATCC51277 or DSM20458. Said free fraction is particularly useful as an immunomodulating agent for a series of pathologies, being further characterized in that it has a high inhibitory effect against the symptoms associated with disorders. The fraction obtained can moreover be formulated in pharmaceutical compositions for local topical use, for example in gels.

8 Claims, 2 Drawing Sheets

PROPIONIBACTERIUM ACNES AND GRANULOSUM PARIETAL FRACTION HAVING IMMUNOMODULATING ACTION

CROSS-REFERENCE TO RELATED APPLICATIONS

This application is a national-stage application under 35 U.S.C. § 371 of PCT Application No. PCT/IB2015/055377, filed Jul. 16, 2015, which claims priority to Italian Patent Application No. MI2014A001298 filed Jul. 16, 2014, which are hereby incorporated by reference in their entirety.

TECHNICAL FIELD

The present invention relates in general terms to a *Propionibacterium acnes* and *granulosum* parietal fraction, obtained by delipidation and controlled crushing of the strain ATCC51277 or DSM20458.

STATE OF THE ART

It is well known that the administration of some bacteria can stimulate a body's immune response. However, administering a whole microorganism causes side effects such as to preclude its use.

Over time it has been noted that bacterial fractions, generally of an insoluble parietal type, derived from some microorganisms, such as, for example, mycobacteria and corynebacteria, are capable of stimulating the immune system, but without generating harmful side effects, such as those that can be found when the whole bacterium is administered (see for example Tian X X et al. Anticancer Res 1999, 237-243; Werner et al. Biomedicine 1975, 440-452).

The isolation of insoluble fractions from *Corynebacterium granulosum* is known in particular; they perform a series of actions on different behaviours of the immune system, such as, inter alia, increasing the antibody response in immunodepressed subjects, increasing the production of cytokines and exerting an antitumour action on grafted tumours. Such fractions can be obtained by delipidation and mechanical crushing of the starting bacteria, as illustrated, for example, by Bizzini et al. In the Asian Pacific Journal of Allergy and Immunology, Vol. 2, No 1, 1984, pp 144-153. Other fractions originating from different bacterial strains have also been isolated (see for example T. Metianu et al. FR80.08976 and IT20658), but in any case the majority of this type of fractions have demonstrated to be effective immunomodulating agents capable of activating an antibody response only if formulated and administered parenterally.

There are also known formulations which comprise suitably functionalized or bioprotected insoluble parietal fractions capable of acting as immunomodulating agents also when administered orally (see for example IT22693). However, this type of fractions requires structural modifications which are generally carried out at the end of the crushing step.

For example, TV2005A000026 describes the functionalization, with chitosan, of an insoluble parietal fraction of *Propionibacterium acnes* obtained from the strain ATCC11827 in order to obtain a bioprotected agent having immunomodulating activity.

There thus remains a need to find a non-specific immunomodulating parietal bacterial fraction that can perform its action even without particular functionalizations and/or bioprotections (for example complexing with a carrier), and is applicable topically, for example in the form of a cream, ointment or gel.

The applicants have now found that it is possible to obtain a parietal fraction endowed with a high immunomodulating activity and having an inhibitory effect on the symptoms associated with disorders by delipidation and controlled crushing of strains ATCC51277 and DSM20458 of *Propionibacterium acnes* and *granulosum*. The free parietal fraction thus obtained can be used in the preparation of a medicament for topical use endowed with a high immunostimulating power and an inhibitory effect on the symptoms of a broad range of pathologies.

AIM OF THE INVENTION

In a first aspect, the invention relates to a free parietal fraction of *Propionibacterium acnes* and *granulosum*, obtained by delipidation and controlled crushing of the strain ATCC51277 or DSM20458.

The chemical composition of said fraction is characterized in that it is composed of parietal peptidoglycans associated with glycoproteins.

In an additional aspect, the invention relates to an aqueous suspension comprising the above-mentioned free parietal fraction. Said aqueous suspension can be used to prepare a pharmaceutical composition for topical use, for example in gel form.

Forming an additional aspect is a pharmaceutical preparation, preferably in gel form, comprising the above-mentioned parietal fraction in a mixture with at least one pharmaceutically acceptable carrier or excipients and having a high non-specific immunomodulating activity and a high inhibitory effect on the symptoms associated with disorders.

In a further aspect, the invention relates to a process for preparing the above-mentioned free parietal fraction, said process comprising the steps of delipidation and controlled crushing of a strain of *Propionibacterium acnes* and *granulosum* selected between ATCC51277 and DSM20458.

In a final aspect, the invention relates to the parietal fraction, or a pharmaceutical preparation thereof, for use as an immunostimulating and/or symptom inhibiting agent, preferably for the treatment of vulvovaginitis caused by *Candida* or of bacterial origin.

DETAILED DESCRIPTION OF PREFERRED EMBODIMENTS OF THE INVENTION

The starting bacteria of the invention, *Propionibacterium acnes* and *granulosum* (belonging to the ATCC and DSM collections and having the numbers 51277 and 20458, respectively), are characterized in that they: have a rod shape, are anaerobic, non-pyrogenic and Gram-positive, produce smooth colonies on agar plates, do not produce indole, do not reduce nitrates, do not generate $H_2S$, produce catalysis, and ferment glucose, but not mannitol or lactose. Said strains can be obtained from LGC Standards and/or Leibniz Institute DSMZ.

The parietal fraction of the present invention shows a high immunomodulating and/or symptom inhibiting activity also if applied topically, without there being any need to carry out further structural modifications or biofunctionalizations, such as, for example, conjugation to a carrier, as is required in the prior art for parietal fractions obtained with similar methods. The applicants have in fact noted that the fraction of the invention, obtained by delipidation and controlled crushing of the strains ATCC51277 or DSM20458, can be conveniently formulated in a composition for topical application directly at the end of the crushing step as described below in detail. The clinical tests conducted by the applicant and included in the experimental part hereof have demonstrated the fact that the parietal fraction of the invention shows a local therapeutic effect, combined with a surprising improvement in symptoms, in particular itching and skin irritations in general. The present fraction is capable of performing its function thanks also to the fact that it is not substantially absorbed by the skin, thus enabling it to exhibit a greater local action and a high inhibition of symptoms.

In example 2, in particular, the immunostimulating activity of the following compounds is compared by means of a phagocytosis test: parietal fraction of the invention, parietal fraction of the invention conjugated with a carrier, 7BVP parietal fraction and 7BVP parietal fraction conjugated with a carrier. From the test it may be observed that the fraction of the invention used as such proves to have the greatest immunostimulating effect. It follows that the decisive advantage of the new fraction lies not only in its greater activity, but also in the fact that it does not require complexing with a carrier, with the risk of inducing structural modifications.

Figure 2:
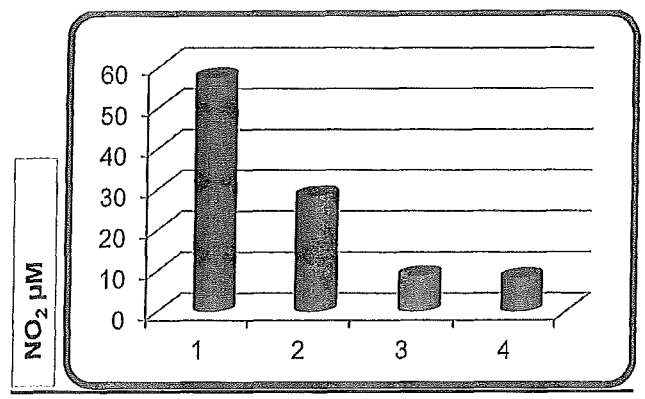
FIG. 2: effect of the fractions 1-4 on the killing activity of macrophages.

It was further verified (using the Griess Reagent System) that the fraction of the invention is capable of enhancing the killing ability of macrophages through an increase in the production of $NO_2$, as indicated for example in FIG. 2.

Thanks to the high activity of the present free parietal fraction it is possible to produce pharmaceutical preparations, for example in gel form, for topical use, at a low dosage and containing small quantities of the active ingredient.

As mentioned above, the *Propionibacterium acnes* and *granulosum* parietal fraction of the invention, having immunomodulating activity, is obtained through a process which comprises delipidation and controlled crushing of the strain ATCC51277 or, preferably, DSM20458.

The applicants have noted that, depending on the experimental conditions used, it is possible to optimize the immunomodulating activity of the fraction obtained. In any case, it is preferable to carry out said steps under controlled conditions, above all as far as the crushing is concerned, in order to obtain a fraction formed by the association of a glycoprotein with a parietal peptidoglycan and having an activity of stimulating the reticuloendothelial system.

In this regard, and according to a preferred embodiment, the delipidation is carried out by treating inactivated, killed *Propionibacterium acnes* and *granulosum* ATCC51277 or DSM20458 bacteria with an alcoholic mixture, preferably ether:ethanol, even more preferably in a 1:1 ratio, for a time comprised between about 8 and 10 hours. At the end of the treatment, the bacteria are treated with chloroform and resuspended in a chloroform:methanol mixture, preferably in a 2:1 ratio. The preliminary steps of inactivating and killing the bacteria can be carried out using methods known in the art, for example by heating and/or treatment with formaldehyde.

Delipidation is particularly useful for favouring the exposure of sites involved in the activity. At the end of delipidation, the bacteria are typically subjected to a drying process, for example by exposure to air, and then subjected to the controlled crushing step.

In this regard, the crushing can take place by sonication or, preferably, by low-speed shaking. Preferred shaking speeds are comprised between 3,000 and 5,000 rpm, more preferably between 3,000 and 3,500 rpm.

Five hundred mg of bacteria is suspended in 20 ml of water in a suitable container. The suspension is made to cool by immersing the container in an ice bath. Crushing follows, with 3 or 4 one- or two-minute cycles. Between one crushing cycle and another, allow the suspension to cool. The crushed walls thus obtained are collected by centrifugation and the salts eliminated by dialysis against water. The final yield of fractions obtained is comprised between about 5 and 15% of the dry weight of the starting bacteria. The maximum obtainable yield is equal to 20%.

It should be noted that the free parietal fraction obtained at the end of the process of the invention substantially maintains the immunomodulating properties of the original bacterial strain unchanged, whilst ensuring, however, the advantages associated with the use of a bacterial fraction (compared to a whole untreated microorganism), such as, for example, the absence of side effects, for example the absence of a pyrogenic effect. Moreover, the fraction thus obtained can be directly used topically without the need for further functionalizations or bioprotections (i.e. in free form), e.g. modifications with chitosan or the like.

In an additional aspect, the invention relates to a pharmaceutical preparation comprising the above-described parietal fraction in a mixture with at least one pharmaceutically acceptable excipient, preferably for topical application. Examples of pharmaceutical preparations of the invention are: unguents, ointments, creams, lotions, foams and preferably gels.

Examples of pharmaceutically acceptable excipients are emollients, gelling agents and the like, typically used in the pharmaceutical field. Preferred examples of excipients used in the pharmaceutical preparation of the invention are the moisturizing agent hyaluronic acid and/or the film-forming/moisturizing agent polycarbophil.

By way of example, the pharmaceutical preparation in gel form of the invention can be made by mixing an aqueous suspension of the fraction of the invention as described above, with a suitable gelling agent, for example selected from among: pectin, gum arabic, isinglass, tragacanth, cellulose derivatives and the like.

Preferably, the pharmaceutical preparation of the invention contains the parietal fraction in an amount of between 0.001 and 0.01% w/w (understood as the weight of the active ingredient relative to the total weight), preferably between 0.001% and 0.005% w/w.

The present parietal fraction, or the associated pharmaceutical composition, is particularly useful as an immunomodulating agent in the treatment of vulvovaginitis of fungal origin (for example caused by *Candida*) and/or bacterial origin, for example caused by *Gardnerella*, in the treatment of viral infections caused by HPV, herpes simplex or zoster, or more in general, in the topical treatment of skin alterations such as dermatitis, actinic keratosis, infections and/or lesions caused by HPV, acne, sunburn and the like. The present fraction is also useful as an antitumour agent.

The use thereof in the topical treatment of fungal and/or bacterial vulvovaginitis or the treatment of actinic keratosis or infections and/or lesions caused by/associated with HPV (human papillomavirus) is particularly preferred.

Thanks to its ease of use and long-lasting local persistence, the immunomodulating action of the present fraction, or the associated pharmaceutical composition, is particularly appreciable, in conjunction with an action of inhibiting symptoms which is already effective only a few minutes after local application, typically in drastically reducing the itching sensation.

The invention will now be described in the following experimental part by way of illustration and therefore not by way of limitation.

EXPERIMENTAL PART

Example 1

Process for Preparing the Immunomodulating Parietal Fraction of the Invention, Originating from Strains of *Propionibacterium acnes* and *Granulosum* (ATCC51277 or DSM20458).

The *Propionibacterium acnes* and *granulosum* ATCC51277 or DSM20458 bacteria are cultured in a fermenter under strict anaerobiosis in a suitable medium and collected at the end of the logarithmic phase according to known procedures. They are then inactivated by heating for 1 hour at 60° C. or by treatment with formaldehyde at a final concentration of 0.1%. The killed bacteria are washed with water and subjected to delipidation in a Soxhlet apparatus by suspension of the bacteria in an ether:ethanol (1:1) mixture for about 8 hours, and subsequent treatments with chloroform for about 8 hours and with a chloroform:methanol (2:1) mixture for about 8 more hours.

The air-dried bacteria are collected and resuspended in water, in proportions of 500 mg of bacteria in 20 ml of water. The suspension is made to cool with ice and subsequently crushed with 3 or 4 Ultra-Turrax cycles at a speed of between 3,000 and 3,500 rpm.

The crushed walls thus obtained are collected by centrifugation and the salts eliminated by dialysis against water. The final yield of fractions obtained is about 15% of the dry weight of the starting bacteria.

Example 2 (Comparative)

Activity of the Parietal Fraction of the Invention Obtained from *Propionibacterium granulosum* Bacteria of Strain DSM2058 in Stimulating Phagocytosis and Killing in J774 Macrophages as Compared to the Parietal Fraction Obtained from *Propionibacterium acnes* Bacteria of Strain ATCC 11827 (7BVP Fraction), 7BVP Fraction Complexed with Chitosan and the Fraction of the Invention Complexed with Chitosan.

Figure 1:
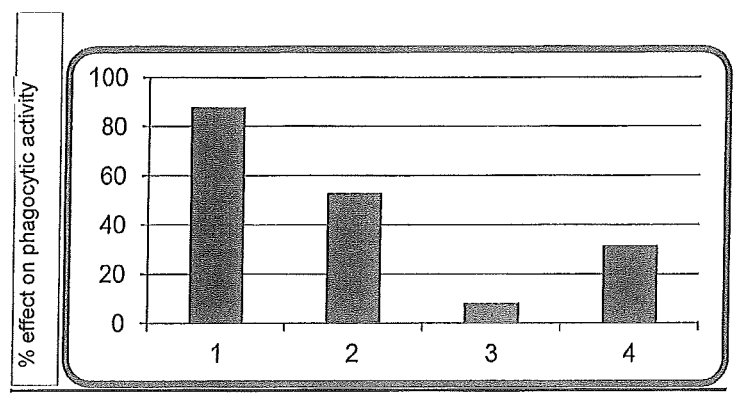
FIG. 1: phagocytic activity of the various parietal fractions, with reference to example 2, wherein: 1. is the *P. granulosum* parietal fraction of the invention; 2. is the *P. granulosum* parietal fraction complexed with chitosan; 3. is the 7BVP fraction; and 4. is the 7BVP fraction complexed with chitosan.

The percentage increase in the phagocytic activity of J774 macrophages of the fraction to which the patent relates was compared with: fraction of the patent complexed with chitosan, 7BVP fraction and 7BVP fraction complexed with chitosan, respectively having the numbering 1,2,3,4 in FIG. 1.

From the figure it may be clearly deduced not only that the fraction in itself is highly active, but also that complexing it with chitosan actually reduces its activity. The opposite behaviour was observed for fraction 3, whose complexing with chitosan (fraction 4) in contrast led to an increase in activity.

The same behaviour occurs with respect to the induction of $NO_2$ production by J774 macrophages after stimulation with different parietal fractions, as such or complexed with chitosan, as shown in FIG. 2.

Example 3

Immunomodulating Activity of a Pharmaceutical Composition of the Invention (Gel) in the Treatment of Candidal or Bacterial Vulvovaginitis After topical vulvovaginal application of a gel containing 0.001% w/w of the parietal fraction of the invention obtained from *Propionibacterium acnes* and *granulosum* DSM20458 or ATCC51277, an immediate reduction is observed in the associated symptoms, such as itching and burning. These symptoms disappear completely after about 5 days of successive applications. It was further verified that the infection that was initially present disappeared after about 5-7 days of treatment.

It was also verified that the topical application of the gel exerts the same effect on *Candida* infections as a treatment with fluconazole 150 mg administered orally.

It was further verified that subjects that do not respond to fluconazole 150 mg respond, in contrast, to treatment with the gel of the example.

It was also verified that the topical application of the gel exerts the same effect on *Gardnerella* infections as a treatment with Clindamycin 2% vaginal cream.

Example 4

Immunomodulating Activity of a Pharmaceutical Composition of the Invention (Gel) in Treatment of Herpes Simplex or Zoster.

A gel containing 0.001% of the parietal fraction of *Propionibacterium acnes* and *granulosum* from strain DSM20458 or ATCC51277 was found to be effective in the treatment of herpes simplex and herpes zoster.

In both cases, its effectiveness was verified in terms of disappearance of the associated symptoms, such as itching and pain and inflammation, following topical application of the gel on the lesions.

Example 5

Immunomodulating Activity of a Pharmaceutical Composition of the Invention (Gel) in the Treatment of Juvenile Acne.

A gel containing 0.001% of the parietal fraction of the invention was found to be effective in the treatment of juvenile acne. The treatment entails daily application of the gel over the whole face. A major regression of inflammation and comedones occurred after about one week of treatment.

Example 6 (Comparative)

Effect of the Present Parietal Fraction in Inhibiting Symptoms Compared to a Fraction Obtained from Another Bacterial Strain.

It was verified that a preparation for topical use (gel) containing 0.001% of the parietal fraction of the patent is active in inhibiting the symptoms associated with candidal infections, such as itching and burning, 5 minutes after application. This result was not obtained with a preparation containing 0.001% of the 7BVP fraction complexed with chitosan, which shows to be effective in inhibiting symptoms only after the third day of treatment.

Example 7

Forty subjects were included in the study. Seven of them did not undergo the second examination for personal reasons and were lost during the follow-up. The remaining 33 subjects underwent the examinations provided for by the study. The reported results refer to the 33 subjects who completed the study.

At the second examination (2), none of the 33 subjects reported any adverse events or intolerance to the treatment. All 33 subjects stated that they carried out the treatment according to the instructions received and reported the daily VAS score during treatment and the unused product. Based on an analysis of the unused product, it was calculated that all 33 subjects had duly carried out the treatment according to the instructions received. An assessment of cultures from vaginal swabs at the first examination (1) showed that in 27 of the subjects included in the study, anaerobic germs characteristic of vulvovaginitis were present in vaginal secretions, whereas in the remaining 6 the culture was negative. In all 33 cases, the vaginal and vulvar symptoms (itching and burning) decreased significantly over the course of the treatment and the reduction was significant starting from the third day of treatment (Table 1), without any significant difference between the subjects who had a positive (group A) or negative (group B) vaginal culture at the $1^{st}$ examination (Table 2).

Vulvar erythema and leucorrhoea were also significantly reduced at the $2^{nd}$ examination compared to the $1^{st}$ examination (Table 1) and there was no difference between the group with a positive (group A) or negative (group B) vaginal swab at the $1^{st}$ examination (Table 2).

The degree of satisfaction was high (6±0.4) (Table 1) and not significantly different between subjects with positive or negative vaginal swabs at the $1^{st}$ examination (5.8±0.4 vs. 5.7±0.30; p>0.05).

At the $2^{nd}$ examination, the vaginal swab was negative in 19 of the 27 subjects who had had a positive vaginal swab at the 1st examination and continued to be negative in the 6 subjects who had previously tested negative at the $1^{st}$ examination.

TABLE II

| | Examination 1 | Examination 2 | SIGNIFICANCE |
|---|---|---|---|
| Vulvar Itching (VAS) | | | |
| GROUP A (27) | 7.3 ± 0.5 | 2.5 ± 0.5* | p > 0.05 |
| GROUP B (6) | 7.3 ± 0.5 | 2.3 ± 0.5* | p > 0.05 |
| Vaginal Itching (VAS) | | | |
| GROUP A (27) | 7.2 ± 0.4 | 2.5 ± 0.5* | p > 0.05 |
| GROUP B (6) | 7.3 ± 0.5 | 2.3 ± 0.5* | p > 0.05 |
| Vulvar Burning (VAS) | | | |
| GROUP A (27) | 7.3 ± 0.4 | 2.5 ± 0.5* | p > 0.05 |
| GROUP B (6) | 7.3 ± 0.5 | 2.3 ± 0.5* | p > 0.05 |
| Vaginal Burning (VAS) | | | |
| GROUP A (27) | 7.2 ± 0.4 | 2.5 ± 0.5* | p > 0.05 |
| GROUP B (6) | 7.3 ± 0.5 | 2.5 ± 0.5* | p > 0.05 |
| LEUCORRHOEA (Score from 1-4) | | | |
| GROUP A (27) | 3.2 ± 0.4 | 1.8 ± 0.6* | p > 0.05 |
| GROUP B (6) | 3.1 ± 0.4 | 1.5 ± 0.5* | p > 0.05 |
| ERYTHEMA (Score from 1-4) | | | |
| GROUP A (27) | 3.2 ± 0.4 | 1.6 ± 0.6* | p > 0.05 |
| GROUP B (6) | 3.1 ± 0.4 | 1.6 ± 0.5* | p > 0.05 |

Considering the (6) subjects with the persistence of a negative swab at the $2^{nd}$ examination plus those (19) with a negative swab at the $2^{nd}$ examination, but a positive one at the $1^{st}$ examination (total negative swabs at the $2^{nd}$ examination: 25) (group D), vs. those (8) with the persistence of a positive swab at the 2nd examination (group C), the results obtained on vulvovaginal symptoms are shown in Table 3.

TABLE III

| | EXAMINATION 1 | EXAMINATION 2 | SIGNIFICANCE |
|---|---|---|---|
| Vulvar Itching (VAS) | | | |
| GROUP C (8) | 7.3 ± 0.5 | 2.2 ± 0.4* | p > 0.05 |
| GROUP D (25) | 7.3 ± 0.4 | 2.5 ± 0.5* | p > 0.05 |
| Vaginal Itching (VAS) | | | |
| GROUP C (8) | 7.3 ± 0.5 | 2.3 ± 0.4* | p > 0.05 |
| GROUP D (25) | 7.2 ± 0.4 | 2.5 ± 0.5* | p > 0.05 |
| Vulvar Burning (VAS) | | | |

TABLE I

| | Prior to treatment Examination 1 | 1st day of treatment | 2nd day of treatment | 3rd day of treatment | 4th day of treatment | 5th day of treatment | 6th day Examination 2 |
|---|---|---|---|---|---|---|---|
| Vulvar Itching (VAS) | 7.3 ± 0.5 | 7.0 ± 0.5 | 6.5 ± 0.5 | 5.4 ± 0.7* | 4.5 ± 0.7* | 3.3 ± 0.5* | 2.5 ± 0.5* |
| Vaginal Itching (VAS) | 7.3 ± 0.4 | 7.1 ± 0.4 | 6.6 ± 0.5 | 5.3 ± 0.7* | 4.5 ± 0.7* | 3.3 ± 0.5* | 2.5 ± 0.5* |
| Vulvar Burning (VAS) | 7.3 ± 0.5 | 7.0 ± 0.3 | 6.5 ± 0.5 | 5.4 ± 0.7* | 4.5 ± 0.7* | 3.3 ± 0.5* | 2.5 ± 0.5* |
| Vaginal Burning (VAS) | 7.2 ± 0.4 | 7.0 ± 0.3 | 6.6 ± 0.5 | 5.4 ± 0.7* | 4.4 ± 0.6* | 3.3 ± 0.6* | 2.5 ± 0.5* |
| Leucorrhoea (Score from 1-4) | 3.2 ± 0.4 | — | — | — | — | — | 1.8 ± 0.5* |
| Erythema (Score from 1-4) | 3.1 ± 0.3 | — | — | — | — | — | 1.6 ± 0.6* |
| Satisfaction (Score from 1-6) | | | | | | | 6.0 ± 0.4 |

TABLE III-continued

|  | EXAMINATION 1 | EXAMINATION 2 | SIGNIFICANCE |
|---|---|---|---|
| GROUP C (8) | 7.3 ± 0.5 | 2.3 ± 0.5* | p > 0.05 |
| GROUP D (25) | 7.2 ± 0.4 | 2.5 ± 0.5* | p > 0.05 |
| Vaginal Burning (VAS) | | | |
| GROUP C (8) | 7.3 ± 0.5 | 2.3 ± 0.5* | p > 0.05 |
| GROUP D (25) | 7.2 ± 0.4 | 2.6 ± 0.5* | p > 0.05 |
| Leucorrhoea (Score from 1-4) | | | |
| GROUP C (8) | 3.3 ± 0.4 | 1.9 ± 0.4* | p > 0.05 |
| GROUP D (25) | 3.1 ± 0.3 | 1.8 ± 0.4* | p > 0.05 |
| Erythema (score from 1-4) | | | |
| GROUP C (8) | 3.4 ± 0.5 | 1.6 ± 0.7* | p > 0.05 |
| GROUP D (25) | 3.1 ± 0.3 | 1.6 ± 0.5* | p > 0.05 |

No significant difference in the reduction of vulvovaginal symptoms, leucorrhoea or erythema was observed between the two groups of subjects (Table 3). The degree of satisfaction was also high and did not differ between the two groups with positive or negative results for the vaginal swab taken at the $2^{nd}$ examination (5.6±0.5 vs. 5.8±0.4; p>0.05). In the group of subjects treated with 2% clindamycin cream (control group), 40 women were recruited and reported the effectiveness, tolerability and satisfaction with the treatment via a phone interview. The results, shown in Table 4, highlight a reduction in symptoms with scores that do not differ from those of the subjects treated with the fraction of the present invention.

TABLE IV

|  | Prior to treatment Examination 1 | 1st day of treatment | 2nd day of treatment | 3rd day of treatment | 4th day of treatment | 5th day of treatment | 6th day telephone interview |
|---|---|---|---|---|---|---|---|
| Vulvar Itching (VAS) | 7.4 ± 0.6 | 7.0 ± 0.6 | 6.8 ± 0.4 | 5.8 ± 0.7* | 450 ± 0.7* | 3.8 ± 0.5* | 2.8 ± 0.6* |
| Vaginal Itching (VAS) | 7.3 ± 0.8 | 7.1 ± 0.7 | 6.8 ± 0.6 | 6.0 ± 0.8* | 5.4 ± 0.8* | 3.6 ± 0.6* | 2.4 ± 0.8* |
| Vulvar Burning (VAS) | 7.2 ± 0.5 | 7.2 ± 0.4 | 6.6 ± 0.6 | 5.8 ± 0.8* | 4.3 ± 0.8* | 3.8 ± 0.6* | 2.6 ± 0.6* |
| Vaginal Burning (VAS) | 7.2 ± 0.4 | 7.1 ± 0.4 | 6.8 ± 0.6 | 5.7 ± 0.7* | 4.6 ± 0.8* | 3.6 ± 0.7* | 2.6 ± 0.6* |
| Satisfaction (Score from 1-6) |  |  |  |  |  |  | 5.5 ± 0.9 |

The results suggest that the parietal fraction of the present invention, when administered locally, is capable of activating the immune system at a local level and is thus effective in antagonizing the growth of anaerobic microorganisms responsible for vulvovaginitis.

With 5 days of treatment, the activation of the immune system at the level of the mucosa served to render the vaginal swab for anaerobic germs negative in 70% of the cases. This was associated with a significant reduction in local symptoms, which prior to treatment showed a VAS score of over 7. The fact that a total disappearance of symptoms was not reported by all subjects is likely to be related to individual variability; however, it should be pointed out that in all treated subjects a significant reduction in subjective and objective symptoms was calculated. This resulted in a high degree of satisfaction among the treated subjects. This emerged not only in subjects in whom the vaginal swab became negative, but also in the remaining subjects, in whom the symptoms decreased significantly.

Example 8

Ten female and male outpatients ranging in age from 18 to 55 years, with HPV lesions evaluated by means of a HPV_DNA test, applied the composition of the present invention once a day on the lesions for 1 month before undergoing surgical removal of the lesions themselves.

Five patients had a total regression of the lesions within the month of treatment and did not undergo a surgical removal procedure.

Three patients had an evident regression of the lesions and were treated with surgical removal to eliminate the residual lesions.

Two patients did not respond to the topical treatment and were treated with surgical removal.

The results demonstrated that the preparation is capable of eliminating and/or favouring a reduction in lesions caused by HPV.

The invention claimed is:

1. A method to modulate immune system response in an individual to reduce itching and/or burning related to *Candida, Gardnerella*, Herpes simplex, Herpes zoster, or juvenile acne, comprising the step of administering an effective amount of the parietal fraction obtained by delipidation and crushing of the strain *Propionibacterium granulosum* deposited with the DSM under the accession number DSM20458 to an individual in need thereof, wherein the administration of the parietal fraction is a topical application being applied to an affected area, wherein the delipidating step is carried out by treating inactivated bacteria with an alcoholic mixture for at least 8-10 hours and the crushing step is carried out by sonication or by shaking.

2. The method according to claim 1, wherein the alcoholic mixture is an ethter:ethanol mixture.

3. The method according to claim 2, wherein the ether:ethanol ratio is 1:1.

4. The method according to claim 1, wherein the crushing step is carried out by sonication at speeds of between 3000 and 5000 rpm.

5. The method according to claim 1, wherein the parietal fraction is present in a pharmaceutical composition mixture that includes at least one acceptable pharmaceutical excipient.

6. The method according to claim 5, wherein the parietal fraction is present in the pharmaceutical composition in amount of 0.001-0.01% w/w.

7. The method according to claim 5, wherein the pharmaceutical composition is formulated as an unguent, ointment, cream, lotion, foam or gel.

8. The method according to claim 5, wherein the pharmaceutical excipient is hyaluronic acid, polycarbophil, or a combination thereof.

* * * * *